United States Patent [19]

Magers et al.

[11] 4,318,984

[45] * Mar. 9, 1982

[54] STABILIZED COMPOSITION, TEST DEVICE, AND METHOD FOR DETECTING THE PRESENCE OF A SUGAR IN A TEST SAMPLE

[75] Inventors: Thomas A. Magers, South Bend; David L. Tabb, Elkhart, both of Ind.

[73] Assignee: Miles Laboratories, Inc., Elkhart, Ind.

[*] Notice: The portion of the term of this patent subsequent to Jul. 21, 1998, has been disclaimed.

[21] Appl. No.: 93,605

[22] Filed: Nov. 13, 1979

[51] Int. Cl.³ .............................................. C12Q 1/54
[52] U.S. Cl. .................... 435/14; 23/230 B; 252/408; 422/56; 435/25; 435/28
[58] Field of Search ........................... 435/14, 25, 28; 23/230 B; 422/56; 252/408

[56] References Cited

U.S. PATENT DOCUMENTS 2,848,308  8/1958  Free ..................................... 435/14
4,071,317  1/1978  Lam ............................. 23/230 B X Primary Examiner—Robert J. Warden
Attorney, Agent, or Firm—Edward H. Gorman, Jr.

[57] ABSTRACT

An improved composition, test device and method for detecting the presence of a sugar in a test sample are disclosed. The composition comprises a sugar oxidase, a peroxidase, a chromogen compound capable of producing a detectable response in the presence of hydrogen peroxide and peroxidase, and an enhancer compound having the structure

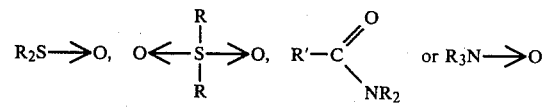

in which the R substituents, same or different, are hydrogen, lower alkyl, lower alkyloxy, aryl or aryloxy; or in which two of the R substituents bound to a common atom together form a closed ring having 3 to about 6 atoms, said ring being saturated, unsaturated or aromatic. R' is hydrogen or an alkyl or alkenyl group having 1 to about 20 carbon atoms. The composition can be incorporated with a carrier matrix to form a test device. The method comprises contacting a test solution with the device and observing any detectable response.

30 Claims, No Drawings

STABILIZED COMPOSITION, TEST DEVICE, AND METHOD FOR DETECTING THE PRESENCE OF A SUGAR IN A TEST SAMPLE

BACKGROUND OF THE INVENTION

1. Field of the Invention

The present invention relates to the field of analysis of a test sample. More particularly, it relates to the analysis of a test sample for the presence of a sugar, such as glucose, fructose, lactose, galactose, mannose, maltose or the pentoses.

The analysis of test samples for the presence of sugars finds utility in many unrelated arts. Thus, the present invention pertains to such diverse technologies as the brewing industry, biochemical research and medical diagnostics. In the brewing industry, for example, starch is converted to sugars, such as maltose, prior to actual fermentation. The presence of maltose is therefore carefully monitored to assure high yields from the grain starting material. Many biochemical systems require glucose in carefully controlled concentrations as their cellular energy source, and the research of such systems necessitates that these concentrations be carefully monitored. The medical profession utilizes sugar analysis to a great extent in diagnosing and controlling such diseases as diabetes mellitus, which manifests itself by abnormally high glucose concentrations in the blood and urine.

Thus, the field of the present invention extends to a very diverse assortment of pursuits. It finds applicability wherever sugar analysis becomes a matter of significance, be it in brewing, the food industry, scientific research or medicine.

2. Description of the Prior Art

The history of sugar analysis is perhaps most noteworthy because it has seen dramatic change over the years, both in the basic chemistries utilized and in its format. For the most part these analyses can be characterized as oxidizing systems which, when reduced, initiate reaction conditions leading to a detectable response, such as a color change or change in wavelength of ultraviolet light absorbed or reflected by the system. Thus, reducing sugars will convert silver oxide to metallic silver, and, if a solution of the sugar is applied to a piece of filter paper impregnated with silver oxide, a black dot develops. F. Feigl, *Chem. Ind.*, Vol. 57, p. 1161, London (1938). Similarly, o-dinitrobenzene and the 3,4- and 3,5-isomers of dinitrophthalic acid give a sensitive color reaction (forming violet shades) when heated with reducing sugars in $Na_2CO_3$. T. Monmose, et al., *Chem. Pharm. Bull. Tokyo*, Vol. 12, p. 14 (1964); F. Feigl, *Spot Tests in Organic Analysis*, 7th Edition, pp. 338–339, Elsevier Publ. Co., New York (1966).

But as early as 1849 it was known that reducing sugars would cause an alkaline solution of $CuSO_4$ to precipitate the yellow to red Copper (I) oxide (or oxyhydrate). H. Fehling, *Ann.*, Vol. 72 (1849). See also B. Herstein, *J. Am. Chem. Soc.*, Vol. 32, p 779 (1910). This early milestone, known as the Fehling test, lent impetus to the development of a far more sensitive test which utilized silver oxide in ammonia, the so-called Tollens reagent, which reacts readily with reducing agents to produce a black precipitate of metallic silver, often forming a mirror on the inside walls of glass reaction vessels. B. Tollens, *Ber.*, Vol. 14, p. 1950 (1881); Vol. 15, p. 1635, 1828 (1882).

Because of the relatively high incidence of *diabetes mellitus* and its accompanying serious clinical consequences, high interest from the biological and medical professions arose in new techniques for analyzing glucose levels in urine and serum. This keen interest led to the development of several new procedures which deviate dramatically from their solution chemistry forbears. These utilize sophisticated biochemical systems which can be incorporated into dry, dip-and-read devices, used in solution or suspension techniques, or in conjunction with spectrophotometers and other hardware.

Of these new techniques, the present invention lends itself to an enzymatic system wherein the analyte (for instance glucose) is a substrate for a particular enzyme, the reaction products being capable of eliciting a detectable response from a family of indicator compounds known loosely in the art as "benzidine-type indicators". These will be more carefully defined, infra, but for the present suffice it to say these compounds undergo color changes in the presence of hydrogen peroxide and the enzyme peroxidase. The glucose/glucose oxidase system exemplifies the prior art, wherein glucose is oxidized to gluconic acid with the concomitant formation of $H_2O_2$ in accordance with

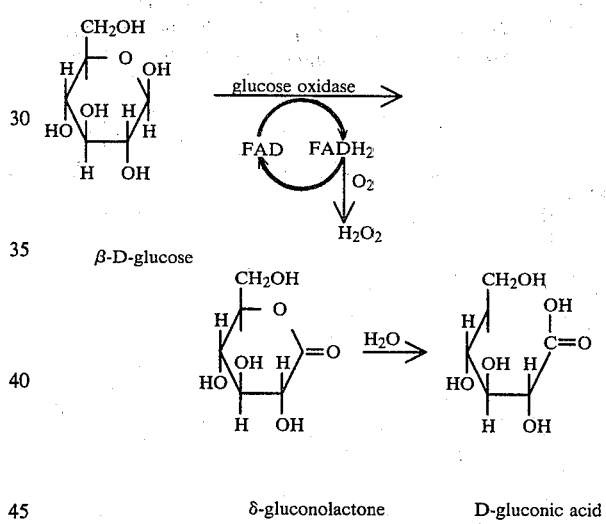

It is the concomitant formation of hydrogen peroxide which facilitates the subsequent, indicator-related steps leading to observable color formation or other detectable response. Thus a benzidine-type indicator responds in the presence of hydrogen peroxide and peroxidase by changing its light absorptive capability.

In practice, this technology is presently utilized for glucose analysis in the form of dip-and-read reagent strips such as those marketed by the Ames Division of Miles Laboratories, Inc. under the trademark CLINISTIX ® and others. Broadly, these comprise a plastic strip, at one end of which is mounted an absorbent paper portion impregnated with the appropriate enzymes, indicator compound and buffering agents as the principal active ingredients. They are used by dipping the reagent-bearing end into the test sample, removing it and comparing any color formed in the paper with a standard color chart calibrated to various glucose concentrations.

Although the mechanism of color formation from benzidine-type indicators in the presence of $H_2O_2$ and peroxidase is not known to a certainty, it is known that two sequentially occurring colorforms result: a first species which is blue in color, and a second which is brown. Because the blue species tends to be transient, ultimately metamorphosing to the brown, it is necessary to look for the color change within a prescribed time period. Otherwise the true significance of color change is lost, as subtle shades of blue—which are easily distinguishable—give way to the less easily interpreted brown hues. The higher the sugar concentration in the test sample, the more aggravated this problem becomes due to the limiting effect on capacity to detect the higher ranges of sugar concentrations. Thus, it can be seen that it is highly advantageous to extend the duration of the blue species, thereby permitting greater differentiation between sugar concentrations, as well as providing higher limits to the detectable concentration ranges.

Moreover, because analytical tools such as reagent strips are not used immediately after manufacture, but are usually stored for relatively long periods, and because too long a period between manufacture and use can result in a loss in efficacy, enhanced shelf life can be a marked asset: the better the shelf life, the more dependable the analytical results.

Thus, the present invention relates to a sugar-sensitive composition utilizing the above-described enzyme/benzidine-type indicator system of the prior art. But the invention goes beyond this system by providing improved stability of the intermediate blue colorform, as well as enhanced storage capability, i.e., shelf life.

Several patents have issued which are deemed pertinent to the present invention. U.S. Pat. No. 2,848,308, issued to Alfred H. Free discloses the basic enzyme chemistry whereby glucose oxidase, peroxidase and a benzidine-type indicator are used in a reagent strip to determine glucose in urine or other bodily fluid. U.S. Pat. No. 3,753,863, issued to Speck discloses the use of lower alkane polyols to "stabilize" indicator solutions of the benzidine type. Finally, U.S. Pat. No. 4,071,317, issued to Lam, discloses the stabilization of an occult blood-sensitive composition through the use of certain sulfone, sulfoxide and amide compounds as diluents during preparation of the composition. This latter composition comprises an organic hydroperoxide compound, and an indicator compound such as of the benzidine type.

To summarize the state of the art prior to the present invention, sugar-sensitive chemistries began to appear on the analytical scene as early as the middle of the 19th century while the advent of Fehling's solution and Tollens' reagent. Most of the "purely chemical" systems which have since emerged have been largely superseded by biochemical systems, particularly those which comprise a sugar oxidase, peroxidase and a peroxide-sensitive indicator of the benzidine type. These latter indicator compounds have been said to be stabilized by the presence of lower alkyl polyols. Finally, a composition sensitive to the presence of occult blood in urine is taught to be stabilized if formulated in the presence of certain sulfone, sulfoxide and/or amide compounds. There is no teaching, to applicants' knowledge, anywhere in the prior art suggesting the presently disclosed and claimed sugar-sensitive composition and test device, or method for their use.

SUMMARY OF THE INVENTION

Briefly stated, the present invention relates to an improved composition, test device and method for determining the presence of a sugar in a test sample. The composition comprises a peroxidase, a sugar oxidase, a chromogen compound of the benzidine type and an enhancer compound having the structure

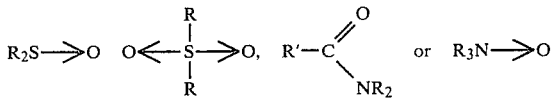

wherein the R substituents, same or different, are hydrogen, lower alkyl, lower alkyloxy, aryl or aryloxy, or in which two of the R substituents bound to a common atom together form a closed ring having 3 to about 6 atoms, said ring being saturated, unsaturated or aromatic; and wherein R' is hydrogen or an alkyl or alkenyl group having 1 to about 20 carbon atoms.

The device of the present invention comprises a carrier matrix incorporated with the composition. The method comprises contacting the test sample with the composition or the device and observing any detectable response.

DETAILED DESCRIPTION OF THE INVENTION

As used in the present specification "lower alkyl" means an alkyl group having from 1 to about 6 carbon atoms, including methyl, ethyl, propyl, isopropyl, cyclopropyl, butyl, isobutyl, t-butyl, cyclobutyl, and all pentyl and hexyl isomers. By "lower alkyloxy" is meant the ether group R-O- wherein R is lower alkyl. By "aryl" is meant phenyl or lower alkyl-substituted phenyl.

The present composition lends itself to a variety of sugar analyses, and can thus be tailored to fill a myriad of needs. Depending on the particular sugar to be assayed, an oxidase is selected which will provide $H_2O_2$ as a reaction product upon oxidation of the sugar. The more specific the oxidase is for its sugar substrate, the more specific will be the resultant assay. As stated supra, this enzymatic technology is useful for many sugars, including glucose, fructose, lactose, galactose, maltose, mannose and the pentoses. Thus, an oxidase specific for the sugar, such as galactose oxidase or glucose oxidase, is utilized. These enzymes are known, as are techniques for their isolation.

The key to providing a detectable response to the presence of the sugar analyte using the sugar oxidase route in the peroxide/benzidine-type indicator combination. Hence the composition of the present invention contains, in addition to an oxidase and a substance having peroxidative activity (such as the enzyme, peroxidase), a benzidine-type chromogenic indicator compound. The term "benzidine-type indicator" is meant to include any compound having the structure

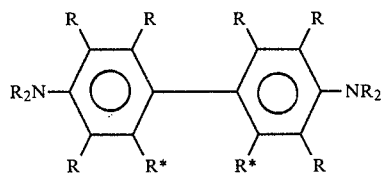

in which R and R*, same or different, are H, lower alkyl, lower alkloxy, aryl, or aryloxy, or in which the substituents R* together comprise $-CH_2-_n$ in which n is 1 or 2. Such compounds include benzidine, o-tolidine, 2,7-diaminofluorene, a 3,3′,5,5′-tetra(loweralkyl)benzidine, such as 3,3′,5,5′-tetramethylbenzidine (hereafter "tetramethylbenzidine"), and the various N-substituted benzidine derivatives.

The enhancer compound of the improved glucose composition can take on four basic structures, as depicted supra. Among those compounds deemed especially suitable are dimethylsulfone, dimethyl sulfoxide, pentamethylene sulfoxide, formamide, N,N-dimethyl formamide, acetamide, N,N-dimethylacetamide, N,N-di($\beta$-hydroxyethyl)acetamide, cocoyldiethanolamide, talloyldiethanolamide, tallowyldiethanolamide, trimethylamine oxide, pyridine-1-oxide, 3-hydroxypyridine-1-oxide, 4-methylpyridine-1-oxide, and 2-chloropyridine-1-oxide. Of course, these by no means represent the entire extent of enhancers within the scope of definition, and others are easily determinable by simple routine laboratory inquiry consistent with the present teachings. Applicants are presently aware of no compounds satisfying the foregoing criteria which do not achieve the effects of improved color stability and enhanced storage capability.

By "cocoyldiethanolamide" is meant the amide of diethanolamine and the fatty acid mixture commercially available as Ninol 2012 Extra manufactured by Stepan Chemical Company of Northfield, Ill. By "talloyldiethanolamide" is meant the amide of diethanolamine and tall oil available as Ninol 1301, and by "tallowyldiethanolamide" is meant the amide of diethanolamine and tallow oil available as Ninol 201, both available from Stepan Chemical Company.

Sugar analysis utilizing the present composition can be achieved in several ways. A solution or suspension of the composition in water or other suitable solvent can be used, whereby a portion of a test sample can be added thereto. Alternatively, a portion of the composition can be added to a spot plate well containing some suspect test sample.

A third way to analyze for sugar is to use a carrier matrix incorporated with the composition. Such a device usually comprises an oblong strip of plastic having mounted at one end a carrier matrix portion incorporated with the composition, the other end of the strip serving as a handle. The plastic strip portion usually measures about 8 by 0.5 cm, the carrier matrix portion having dimensions of about 0.5 by 0.5 cm., although these dimensions are by no means critical.

The carrier matrix utilized in forming the test device can take on a multitude of forms. Thus, U.S. Pat. No. 3,846,247 teaches the use of felt, porous ceramic strips, and woven or matted glass fibers. Additionally, U.S. Pat. No. 3,552,928 teaches the use of wood sticks, cloth, sponge material, and argillaceous substances. The use of synthetic resin fleeces and glass fiber felts as a carrier matrix is suggested in British Pat. No. 1,369,139. Another British Pat. No. 1,349,623, proposes the use of light-permeable meshwork of thin filaments as a cover for an underlying paper matrix. Polyamide fibers are taught in French Pat. No. 2,170,397. These suggestions notwithstanding, however, the material predominantly used in the art as a carrier matrix, and that which is especially suitable for the present invention, is a bibulous paper such as filter paper. It can thus be seen that there is a great deal of leeway in selecting an appropriate material for use as a carrier matrix, and the matrix can take on various physical forms. All of these types are intended as being within the scope of the present invention.

The test composition can be incorporated with a carrier matrix in several ways known to a person of reasonable skill in the art. One way is to pass a web of the carrier matrix material through an impregnating bath containing the test composition ingredients so that the matrix becomes thoroughly saturated with impregnating solution. The saturated matrix is then dried, as in an air oven at 50° C., leaving the test composition incorporated with the matrix.

In order to more clearly elucidate the present invention, as well as to set forth presently preferred embodiments, the following Examples are provided. It is to be understood, however, that the Examples are intended as purely illustrative in nature, and are not intended as limiting in any way.

EXAMPLES I–XII

Various Enhancer Compounds and Their Effects on a Glucose-Sensitive Reagent System Experiments were conducted using a glucose-sensitive reagent system comprising glucose oxidase, peroxidase, and o-tolidine in water. To aliquots of this mixture were added equal weights of various enhancer compounds, one aliquot serving as a control.

The basic reagent system contained the following ingredients:

| | |
|---|---|
| o-tolidine . 2HCl | 0.50 grams (g) |
| poly(vinylpyrrolidone) (10% by weight in water) | 60.0 milliliters (ml) |
| ON 870 polyethoxylated fatty alcohol (General Aniline & Film Corp.) | 0.50 g |
| ethanol (denatured with 5ml. methanol per 100 ml) | 36.0 ml |
| tris buffer* | 47.0 ml |
| *A mixture consisting of: | |
| water | 208.0 ml |
| tris-hydroxymethylaminomethane (Fisher Scientific) | 22.5 g |
| trisodium citrate | 27.2 g |
| glutamic acid | 27.0 g |
| citric acid | 6.16 g |
| Gantrez AN-139 (copolymer of maleic anhydride and vinyl ether obtained from G.A.F. Corporation) (10% by weight in water) | 15.0 ml |
| ascorbic acid (10% by weight in water) | 0.5 ml |
| glucose oxidase in water (5000 I.U. per ml, available from the Marschall Division of Miles Laboratories, Inc.) | 15.0 ml |
| horseradish peroxidase (68 I.U. per milligram, available from Miles Laboratories, Inc.) | 0.50 g |
| distilled water | 26.5 milligrams (mg) |

The resulting mixture was divided into 12 aliquots, 19 ml each, and to 11 of these aliquots were respectively added 0.1 g of the specific enhancer compounds set forth in Table I, the 12th aliquot serving as a control. A 1.0 ml portion of each prepared aliquot, as well as of the control with no enhancer, were respectively placed in separate wells of a spot plate. To each portion was then added a small amount of an aqueous solution of glucose (1.0% by weight in water), by adding an initial 1 microliter ($\mu$l) dose, observing any color formation and the time it took to appear, and then continuing to add glucose to determine the total amount necessary to bring about the occurrence of brown coloration in the spot plate well. Glucose addition was performed using a calibrated syringe (Hamilton Series No. 700, 10 μl capacity). The 1 μl quantity was added instantaneously. No more glucose was added until the time for blue color formation was noted. The additional glucose was then added, in each case, in less than 60 seconds.

TABLE I

| Example | Enhancer Additive | Initial Blue Color formation (1 μl glucose) | Glucose Required Before Browning |
|---|---|---|---|
| I | control | Blue ring formed around edge of well after 60 sec. | 20 μl |
| II | Ninol 1301* | Blue ring after 30 sec. | 70 μl |
| III | Ninol 2012 Extra* | blue flecks - immediate | 90 μl |
| IV | Urea | surface blue - 60 sec. | 30 μl |
| V | N,N-dimethylformamide | blue flecks - immediate | 70 μl |
| VI | Dimethylsulfone | blue flecks - immediate | 68 μl |
| VII | Dimethylsulfoxide | blue surface - 10 sec. | 50 μl |
| VIII | Tetramethylene sulfone | blue surface - 10 sec. | 80 μl |
| IX | 4-methylpyridine-1-oxide | surface blue - 7 sec. | 35 μl |
| X | 3-hydroxypyridine-1-oxide | surface blue - 7 sec. | 42 μl |
| XI | 2-chloropyridine-1-oxide | blue ring after 5 sec. | 45 μl |
| XII | Trimethylamine oxide | surface blue - 5 sec. | 28 μl |

*Stepan Chemical Company, Northfield, Illinois

Table I shows performance data for eleven formulations of the presently claimed composition and of the control. Each enhancer compound tested resulted in a marked improvement over the standard glucose formulation. Thus, Examples II-XII (the present invention) exhibited initial blue color formation upon initial glucose innoculation after only 0-10 seconds (urea, being an exception, taking 60 seconds, see Example IV); whereas in Example I (control) with no additive, initial blue color formation occurred only after 60 seconds. The data demonstrates that the enhancer compounds markedly increase the sensitivity of the control system to small glucose concentrations.

Table I presents still further unexpected beneficial results. The data relating to the formation of the brown colorform of o-tolidine (right column) shows that this undesirable indicator manifestation is dramatically forestalled when one of the claimed enhancers is present, whereas the control data shows browning after addition of a relatively small amount of glucose. Thus, in Example I (control) browning occurred after 20 μl of the glucose solution had been added, whereas in Examples II-XII browning occurred only after 30-90 μl of the glucose solution were added.

To summarize the significance of Examples I-XII, the enhancers improved the present state-of-the-art reagent for glucose determination by (a) causing the initial blue color to form more rapidly, thus demonstrating improved sensitivity to low concentrations of glucose; and (b) delaying the onset of undesirable brown color formation until the addition of much greater amounts of glucose. The enhancers improved the control formulation response to both high and low glucose concentrations.

EXAMPLES XIII-XXIV

Test Devices Prepared from the Compositions of Examples I-XII

The 12 aliquots described supra, and which comprised the solutions used in Examples I-XII were used to prepare test devices. Each device comprised a strip of Trycite (polystyrene) measuring about 8×0.5 cm, to one end of which was affixed a square of Eaton and Dikeman 204 filter paper measuring 0.5×0.5 cm. This paper carrier matrix was affixed to the Trycite using Double-Stick, a double-faced adhesive tape available from 3M Company. Once thus prepared, a separate set of strips was dipped into each solution of Examples I-XII and dried at 50° C. in an air oven for about ten minutes, thus forming a control test device (reagent of Example I) and eleven sets of test devices of the present invention (reagents of Examples II-XII).

Each set of reagent-bearing devices was then tested by dipping the reagent portions thereof respectively into glucose test solutions of different concentrations to ascertain threshold glucose concentrations of the appearance of the blue and brown colorforms of the o-tolidine indicator. For this purpose, test solutions of glucose in water having concentrations of 0, 10, 20, 30, 40, 50, 100, 250, 500, 1000, 2000 and 5000 milligrams glucose per deciliter (mg/dl) were used. The performance data for the respective sets of test devices is presented in Table II.

TABLE II

| Example | Enhancer | Threshold Glucose Concentration - Blue (mg/dl) | Threshold Glucose Concentration - Brown (mg/dl) |
|---|---|---|---|
| XIII | control | (20-30) very slightly blue | (1000) |
| XIV | Ninol 1301 | (20) very light blue | (5000) |
| XV | Ninol 2012 Extra | (20) light blue | midnight blue @ 5000 mg/dl |
| XVI | Urea | (20) blue | (2000) |
| XVII | N,N-Dimethylformamide | (20) peacock blue | (2000) |
| XVIII | Dimethylsulfone | (20) medium blue | (5000) |
| XIX | Dimethylsulfoxide | (20) medium blue | (2000) |
| XX | Tetramethylene sulfone | (20) royal blue | midnight blue @ 5000 mg/dl |
| XXI | 4-methylpyridine-1-oxide | (30) light blue | (2000) |
| XXII | 3-hydroxypyridine-1-oxide | (30) medium blue | (5000) |
| XXIII | 2-chloropyridine-1-oxide | (30) medium blue | midnight blue @ 5000 mg/dl |
| XXIV | Trimethylamine oxide | (30) light blue | (1000) |

The data of Table II clearly shows that a greatly improved glucose-sensitive test device results upon use of the presently claimed enhancers. The control devices of Example XIII exhibited a barely discernible blue tint when dipped into the 20 mg/dl glucose solution and began to brown at 1000 mg/dl glucose. All of the other sets of devices (Examples XIV-XXIV) performed better. For example, when Ninol 2012 Extra, 2-chloropyridine-1-oxide, and tetramethylene sulfone (Examples XV, XXIII, and XX, respectively) were added to the formulation, brown color never occurred, even at a glucose concentration of 5000 mg/dl. Moreover, the initial blue occurring with the devices of Examples XIV–XXIV were invariably darker than that of Example XIII, the control. In every case where the reagent formulation contained an enhancer the resultant device displayed better sensitivity to low glucose concentration, greater blue color stability at high glucose concentrations, or both.

What is claimed is:

1. In a composition for detecting the presence of a sugar in a test sample, wherein said composition comprises a peroxidase, a sugar oxidase and a chromogen compound having the structure

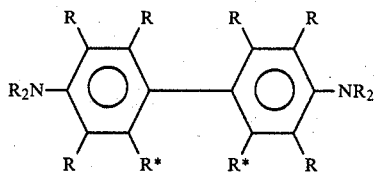

in which R and R*, same or different, are H, lower alkyl, lower alkyloxy, aryl, or aryloxy, or in which the substituents R* together comprise —CH$_2$—$_n$ in which n is 1 or 2;

the improvement wherein said composition further comprises an enhancer compound having the structure

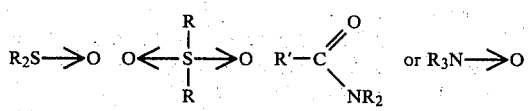

in which the R substituents, same or different, are as described above; or in which two of said R substituents bound to a common atom together form a closed ring having 3 to about 6 atoms, said ring being saturated, unsaturated, or aromatic; and in which R' is hydrogen or an alkyl or alkenyl group having 1 to about 20 carbon atoms.

2. The improved composition of claim 1 wherein said enhancer compound is R$_2$S→O.

3. The improved composition of claim 1 wherein said enhancer compound is

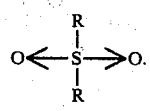

4. The improved composition of claim 1 wherein said enhancer compound is

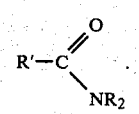

5. The improved composition of claim 1 wherein said enhancer compound is R$_3$N→O.

6. The improved composition of claim 1 wherein said enhancer compound is dimethyl sulfone, dimethyl sulfoxide, pentamethylene sulfoxide, formamide, N,N-dimethyl formamide, acetamide, N,N-dimethylacetamide, N-N-di(β-hydroxyethyl) acetamide, cocoyldiethanolamide, talloyldiethanolamide, tallowyldiethanolamide, trimethylamine oxide, pyridine-1-oxide, 3-hydroxypyridine-1-oxide, 4-methylpyridine-1-oxide, or 2-chloropyridine-1-oxide.

7. The improved composition of any of claims 1–5 or 6 wherein said sugar is glucose and said sugar oxidase is glucose oxidase.

8. The improved composition of any of claims 1–5 or 6 wherein said chromogen compound is o-tolidine.

9. The improved composition of any of claims 1–5 or 6 wherein said chromogen compound is tetramethylbenzidine.

10. The improved composition of any of claims 1–5 or 6 wherein said chromogen compound is 2,7-diaminofluorene.

11. In a test device for detecting the presence of a sugar in a test sample, wherein said device comprises a carrier matrix incorporated with a peroxidase, a sugar oxidase and a chromogen compound having the structure

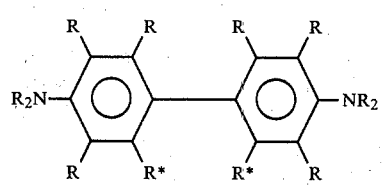

in which R and R*, same or different, are hydrogen, lower alkyl, lower alkyloxy, aryl, or aryloxy, or in which the substituents R* together comprise —CH$_2$—$_n$ in which n is 1 or 2;

the improvement wherein said carrier matrix is additionally incorporated with an enhancer compound having the structure

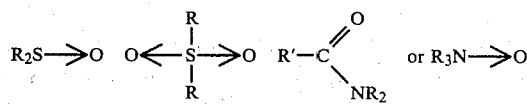

in which the R substituents, same or different, are as recited above; or in which two of said R substituents bound to a common atom together form a closed ring having 3 to about 6 atoms, said ring being saturated, unsaturated, or aromatic, and in which R' is hydrogen or an alkyl or alkenyl group having from 1 to about 20 carbon atoms.

12. The improved test device of claim 11 wherein said enhancer compound is R$_2$S→O.

13. The improved test device of claim 11 wherein said enhancer compound is

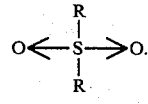

14. The improved test device of claim 11 wherein said enhancer compound is

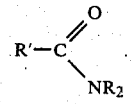

15. The improved test device of claim 11 wherein said enhancer compound is R$_3$N→O.

16. The improved test device of claim 11 wherein said enhancer compound is dimethyl sulfone, dimethyl sulfoxide, pentamethylene sulfoxide, formamide, N,N-dimethyl formamide, acetamide, N,N-dimethylacetamide, N,N-di($\beta$-hydroxyethyl) acetamide, cocoyldiethanolamide, talloyldiethanolamide, tallowyldiethanolamide, trimethylamine oxide, pyridine-1-oxide, 3-hydroxypyridine-1-oxide, 4methylpyridine-1-oxide, or 2-chloropyridine-1-oxide.

17. The improved test device of any of claims 11–15 or 16 wherein said sugar is glucose and said sugar oxidase is glucose oxidase.

18. The improved test device of any of claims 11–15 or 16 wherein said chromogen compound is o-tolidine.

19. The improved test device of any of claims 11–15 or 16 wherein said chromogen compound is tetramethylbenzidine.

20. The improved test device of any of claims 11–15 or 16 wherein said chromogen compound is 2,7-diaminofluorene.

21. A method for detecting the presence of a sugar in a test sample, said method comprising contacting said sample with a test device comprising a carrier matrix incorporated with a peroxidase,
a sugar oxidase,
a chromogen compound having the structure

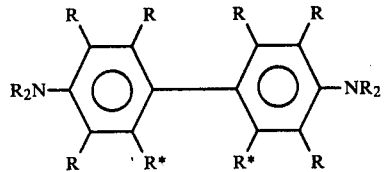

in which the substituents R and R*, same or different, are hydrogen, lower alkyl, lower alkyloxy, aryl, or aryloxy, or in which the R* substituents together comprise —CH$_2$—$_n$ in which n is 1 or 2; and an enhancer compound having the structure

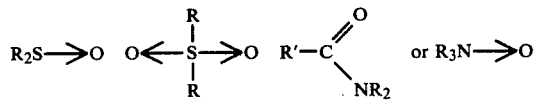

in which the R substituents, same or different, are as recited above, or in which two of said R substituents bound to a common atom together form a closed ring, having 3 to about 6 atoms, said ring being saturated, unsaturated, or aromatic; and in which R' is hydrogen or an alkyl or alkenyl group having from 1 to about 20 carbon atoms; and observing a detectable response produced by said test device.

22. The method of claim 21 wherein said enhancer compound is R$_2$S→O.

23. The method of claim 21 wherein said enhancer compound is

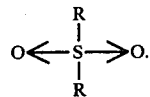

24. The method of claim 21 wherein said enhancer compound is

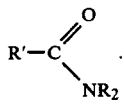

25. The method of claim 21 wherein said enhancer compound is R$_3$N→0.

26. The method of claim 21 wherein said enhancer compound is dimethyl sulfone, dimethyl sulfoxide, pentamethylene sulfoxide, formamide, N,N-dimethyl formamide, acetamide, N,N-dimethylacetamide, N,N-di($\beta$-hydroxyethyl) acetamide, cocoyldiethanolamide, talloyldiethanolamide, tallowyldiethanolamide, trimethylamine oxide, pyridine-1-oxide, 3-hydroxypyridine-1-oxide, 4-methylpyridine-1-oxide, or 2-chloropyridine-1-oxide.

27. The method of any of claims 21–25 or 26 wherein said sugar is glucose and said sugar oxidase is glucose oxidase.

28. The method of any of claims 21–25 or 26 wherein said chromogen compound is o-tolidine.

29. The method of any of claims 21–25 or 26 wherein said chromogen compound is tetramethylbenzidine.

30. The method of any of claims 21–25 or 26 wherein said chromogen compound is 2,7-diaminofluorene.

* * * * *

UNITED STATES PATENT AND TRADEMARK OFFICE
CERTIFICATE OF CORRECTION

PATENT NO. : 4,318,984
DATED : March 9, 1982
INVENTOR(S) : Thomas A. Magers & David L. Tabb It is certified that error appears in the above-identified patent and that said Letters Patent are hereby corrected as shown below:

Col. 4, Line 67, "$-CH_2-_n$" should read -- $\{CH_2\}_n$ --.

Claim 1, line 23 "$-CH_2-_n$" should read -- $\{CH_2\}_n$ --.

Claim 11, line 13 "$-CH_2-_n$" should read -- $\{CH_2\}_n$ --.

Signed and Sealed this

First Day of June 1982

[SEAL]

Attest:

GERALD J. MOSSINGHOFF

Attesting Officer　　Commissioner of Patents and Trademarks